US007240446B2

(12) United States Patent
Bekker

(10) Patent No.: US 7,240,446 B2
(45) Date of Patent: Jul. 10, 2007

(54) IDENTIFICATION BRACELET WITH SEALABLE WINDOW

(75) Inventor: Alexander Bekker, Los Angeles, CA (US)

(73) Assignee: Precision Dynamics Corporation, San Fernando, CA (US)

( * ) Notice: Subject to any disclaimer, the term of this patent is extended or adjusted under 35 U.S.C. 154(b) by 332 days.

(21) Appl. No.: 10/907,852

(22) Filed: Apr. 18, 2005

(65) Prior Publication Data

US 2006/0230661 A1 Oct. 19, 2006

(51) Int. Cl.
*A44C 5/00* (2006.01)
*A61B 5/103* (2006.01)
*A61B 5/117* (2006.01)

(52) U.S. Cl. .......................................................... 40/633

(58) Field of Classification Search .................. 40/633, 40/773; 283/75, 900

See application file for complete search history.

(56) References Cited

U.S. PATENT DOCUMENTS 1,427,891 A * 9/1922 Ziegler ........................ 40/633
2,871,592 A * 2/1959 Polzin ......................... 40/633
3,197,899 A 8/1965 Twentier
3,810,566 A * 5/1974 Adams et al. ................ 40/709
4,199,882 A * 4/1980 Clayman ..................... 40/633
4,221,063 A 9/1980 Charles et al.
4,285,146 A 8/1981 Charles et al.
4,311,740 A * 1/1982 Kay ............................ 428/43
4,318,234 A 3/1982 Charles et al.
4,386,795 A 6/1983 Charles et al.
4,807,807 A * 2/1989 Glick ........................ 229/92.8
4,914,843 A * 4/1990 DeWoskin ................... 40/633
5,581,924 A 12/1996 Peterson
5,740,623 A 4/1998 Juhan et al.
6,546,656 B2 4/2003 Twentier

* cited by examiner

*Primary Examiner*—Lesley D Morris
*Assistant Examiner*—Christopher E Veraa
(74) *Attorney, Agent, or Firm*—Kelly Lowry & Kelley LLP

(57) ABSTRACT

An identification bracelet for mounting about a person's wrist or the like incorporates a sealable window to protect wearer-related information against contact with moisture and the like. The bracelet includes a flexible band defining an information-bearing zone, in combination with an overlying adhesive-backed transparent cover strip. In an initial state, the cover strip has opposite ends securely adhered to the band, and a central window segment separated from the band by a peel-off release film. The window segment is adapted for lift-away separation from the band as by tearing along a line of weakness line at one end thereof to expose the information-bearing zone for receiving wearer-related information, and for facilitated peel-off removal of the release film, followed by adhesively seating the strip central window segment onto the band in a manner defining a sealed perimeter overlying and protecting the wearer-related information.

47 Claims, 8 Drawing Sheets

IDENTIFICATION BRACELET WITH SEALABLE WINDOW

BACKGROUND OF THE INVENTION

This invention relates generally to improvements in identification appliances such as wristbands and the like for mounting onto a specific person or object, and for carrying information associated with the specific band wearer. More particularly, this invention relates to an improved identification bracelet having a sealable window for overlying and protecting wearer-related information applied to or carried by the bracelet against contact with moisture and the like for an extended period of time, wherein such moisture contact could otherwise interfere with or adversely impact human and/or machine reading of the wearer-related information.

Bracelet-type identification appliances such as wristbands and the like are commonly worn by individual patients in a hospital or other medical facility. The identification bracelet normally carries certain human-readable patient identification information such as patient name, room number, patient identification (ID) number, etc., wherein this identification information can be printed directly onto the bracelet, or otherwise applied to a card, tag or label that is affixed to or suitably carried by the bracelet. In addition, a variety of machine-readable information may be similarly applied to or carried by the bracelet, such as bar code information which may duplicate the human-readable patient identification information but may also include selected patient condition information. In recent years, such identification bracelets have also incorporated radio frequency identification (RFID) circuits having the capacity to receive and store significant patient medical history in addition to patent identification and condition information. Such identification bracelets have also been used in a wide range of non-medical environments.

Moisture contact with the wearer-related information carried by the identification bracelet can interfere with and thereby prevent accurate reading thereof by human or automated means. In this regard, some bracelet designs have incorporated a transparent window element to overlie and thereby provide some protection for wearer-related information visible through the transparent window. For example, U.S. Pat. Nos. 4,221,063; 4,285,146; 4,318,234; 4,386,795; and 5,581,924 depict a bracelet wherein a transparent window element cooperates with an underlying band to define a small slotted pocket for slide-fit reception of a card, tag or label having the wearer-related information printed thereon and viewable through the window element. However, many of these bracelet designs provide only limited protection, and, more specifically, are not sealed against water intrusion upon immersion of the bracelet as may occur, for example, during bathing.

Alternative bracelet configurations have been proposed wherein the transparent window element is backed with a transparent, typically pressure-sensitive adhesive layer. See, for example, U.S. Pat. Nos. 3,197,899 and 6,546,656 which depict the transparent window element adhesively positioned over an information-bearing zone or region formed on or carried by an underlying flexible band. The transparent window element is initially adhered at one end to the underlying band and thus comprises a movable flap that can be lifted to expose the information-bearing zone, and further to permit a peel-off film to be removed from the flap before downward displacement into adhered relation with the band in a position overlying the information-bearing zone. Hermetic sealing of the periphery of the information-bearing zone, however, is at best limited to provide minimal protection against water intrusion. In addition, in these bracelet designs, the movable flap is incompatible with convenient and economical manufacturing methods particularly such as producing a plurality of ready-to-use bracelets in a snap-apart or break-apart sheet form. Moreover, the transparent window element in these designs is combined with fastener means for adhesively mounting the bracelet about the wearer's wrist or the like, resulting in a complex bracelet construction with limited inherent variable size adjustment capability.

U.S. Pat. No. 5,740,623 describes another alternative bracelet construction including a tubular band formed from transparent plastic, and defining an internal pocket for slide-fit reception of an information-bearing card, tag or label, with a connector element provided for press-fit reception into the opposite ends of the band to form and retain the band into a closed loop configuration wrapped about a person's wrist or the like. While this bracelet design may provide improved hermetic protection against ingress or moisture or other liquids into contact with the information-bearing card or the like, the tubular band construction does not provide inherent size adjustment capability. In addition, the tubular band construction is also not susceptible to convenient and economical manufacturing methods particularly such as producing a plurality of ready-to-use bracelets in snap-apart or break-apart sheet form.

There exists, therefore, a significant need for further improvements in and to identification bracelets of the type used in a medical facility and the like, particularly wherein a transparent window element is mounted onto an underlying flexible band in a manner conducive to economical manufacture in multi-bracelet sheet form, and further wherein a transparent window element is adapted to overlie and hermetically seal underlying wearer-related information against contact with moisture and the like. The present invention fulfills these needs and provides further related advantages.

SUMMARY OF THE INVENTION

In accordance with the invention, an improved identification bracelet is provided for mounting about a person's wrist or the like, and includes a sealable window to protect wearer-related information against potentially damaging contact with moisture and the like, wherein such moisture contact can interfere with or adversely impact human and/or machine reading of the wearer-related information. The improved bracelet is designed for economical manufacture in a convenient sheet form including multiple bracelets adapted for snap-apart separation from the sheet in a ready-to-use state, or in an end-to-end roll form.

In one preferred form, the identification bracelet comprises an elongated flexible band constructed from a moisture-resistant material to include an information-bearing zone adapted to receive and support wearer-related information such as information printed or written directly thereon, or information applied to a card, tag or label positioned thereon. A transparent, adhesive-backed cover strip spans the information-bearing zone in overlying relation thereto, with opposite ends of the cover strip securely adhered to the underlying band generally at opposite ends of the information-bearing zone. This central window segment is initially separated or easily separable from the underlying band, as by means of a peel-off release film on the underside of the cover strip.

At the time of use, one end of the cover strip central window segment is adapted for lift-away separation from the flexible band, as by tearing the cover strip along a line of weakness such as a perforation line formed therein at a position generally overlying one end of the information-bearing zone on the band. This now-separated end of the cover strip central window segment can be raised relative to the flexible band to expose the information-bearing zone for receiving the wearer-related information, and also for exposing the release film on the underside of the central window segment for peel-off removal. The central window segment can then be pressed downwardly onto the band, into firmly seated and sealed adherence therewith. The cover strip central window segment and the flexible band cooperatively define an hermetically sealed perimeter circumscribing the wearer-related information to safeguard such information against subsequent contact with moisture and the like, thereby safeguarding the information for reliable and accurate reading by human and/or machine means.

The identification bracelet further includes fastener means for retaining the elongated band in a closed loop configuration of selected diametric size wrapped about the wrist or the like of a person or object associated therewith. In one preferred form, the fastener means includes interengageable fastener elements at opposite ends of the flexible band, and preferably independent of the information-bearing zone on the band, such as snap-fit engageable male and female components at one end of the band for engagement with one of a longitudinally spaced-apart series of fastener ports formed in the other end of the band, as disclosed in U.S. Pat. No. 5,581,924 which is incorporated by reference herein. Alternative fastening elements such as adhesive fastening means and the like may be used.

Other features and advantages of the invention will become more apparent from the following detailed description, taken in conjunction with the accompanying drawings which illustrate, by way of example, the principles of the invention.

BRIEF DESCRIPTION OF THE DRAWINGS

The accompanying drawings illustrate the invention. In such drawings:

FIG. 8 is a top perspective view illustrating sealed seating of the adhesive-backed cover strip onto the flexible band in overlying relation to the identification card, tag or label, and further with a perimeter region of the cover strip in adhesively sealed engagement with a perimeter region of the information-bearing zone on the flexible band to define a sealed window protecting the identification card, tag or label against contact with moisture or the like;

DETAILED DESCRIPTION OF THE PREFERRED EMBODIMENT

Figure 12:
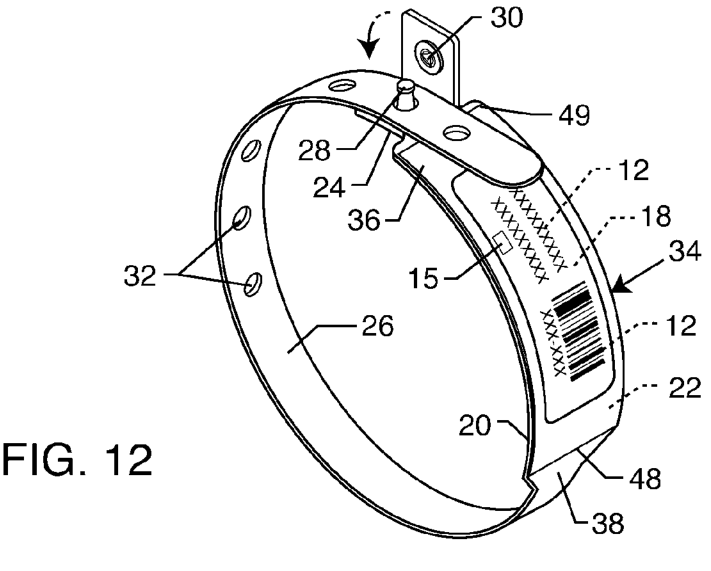
FIG. 12 is a perspective view showing the assembled identification bracelet oriented in a closed loop configuration for mounting about a person's wrist or the like, and further illustrating a fastener for retaining the bracelet in the closed loop configuration of desired diametric size.

As shown in the exemplary drawings, an improved identification bracelet referred to generally by the reference numeral 10 is provided for mounting in a closed loop configuration (FIG. 12) about the wrist or the like of a person or object associated therewith, wherein the bracelet 10 includes or carries wearer-related information 12 (FIGS. 5-9 and 12) associated with the specific person or object. The wearer-related information 12 may be provided in human-readable and/or machine-readable form, and, in accordance with a primary aspect of the invention, is protectively encased within a sealed window where it is safeguarded against contact with moisture and the like. The improved bracelet 10 has a construction suitable for convenient and economical manufacture in a sheet assembly or form 14 (FIG. 1) including multiple bracelets 10 adapted for snap-apart or tear-off separation from the form 14 in a ready-to-use state.

Information-bearing identification bracelets and the like are widely used in a number of applications wherein a convenient and lightweight, relatively inobtrusive identification appliance is desired for use in verifying the identity and/or other key information pertaining to a person or object to whom the bracelet is attached. As one key example, such identification bracelets are well known for use in a hospital or other medical facility to identify an individual patient. That is, wearer-related information such as patient name, etc., is applied to the bracelet which is then affixed about the wrist or the like of the associated patient. The wearer-related information may be applied in human-readable written, typed or printed form, and/or such information may be applied in a machine-readable format such as bar code or by means of memory circuits such as radio frequency identification (RFID) devices. The use of machine-readable formats beneficially expands the volume and type of information, such as patient medical records and/or patient condition information, that can be inputted to and subsequently read from the identification bracelet.

The improved identification bracelet 10 of the present invention beneficially accommodates a wide range of wearer-related information applied directly to the bracelet, or otherwise mounted onto the bracelet as by means of a card, tag or label 18 (FIGS. 5-9 and 11-12), including human-readable and/or machine-readable formats applied thereto by suitable printing methods, such as laser printing, while effectively safeguarding the wearer-related information against potentially damaging contact with moisture and other liquids including solvents and the like, as well as potentially damaging contact with abrasive surfaces, to which the bracelet may be exposed in the course of normal, typically multi-day usage cycle. In the example of an identification bracelet used by a medical patient, the patient may be required to shower or bathe, or otherwise be subjected to various liquids in the course of a hospital stay and related treatment regimen. Moisture contact with the wearer-related information can cause written information to loose clarity, and can interfere with operation of electronic memory circuits, resulting in interference with and/or prevention of information read-out by human or machine methods. The present invention safeguards the wearer-related information against contact with moisture or the like, in a bracelet construction that is suitable for economical manufacture and convenient use, and is compatible with existing facility procedures for printing cards, tags or labels. As shown in FIGS. 5-9 and 12, the machine-readable information may bar code information printed directly onto the bracelet, or printed onto the card, tag or label 18, and/or an RFID device or chip 15 mounted onto the bracelet or alternately onto the card, tag or label 18.

Figure 2:
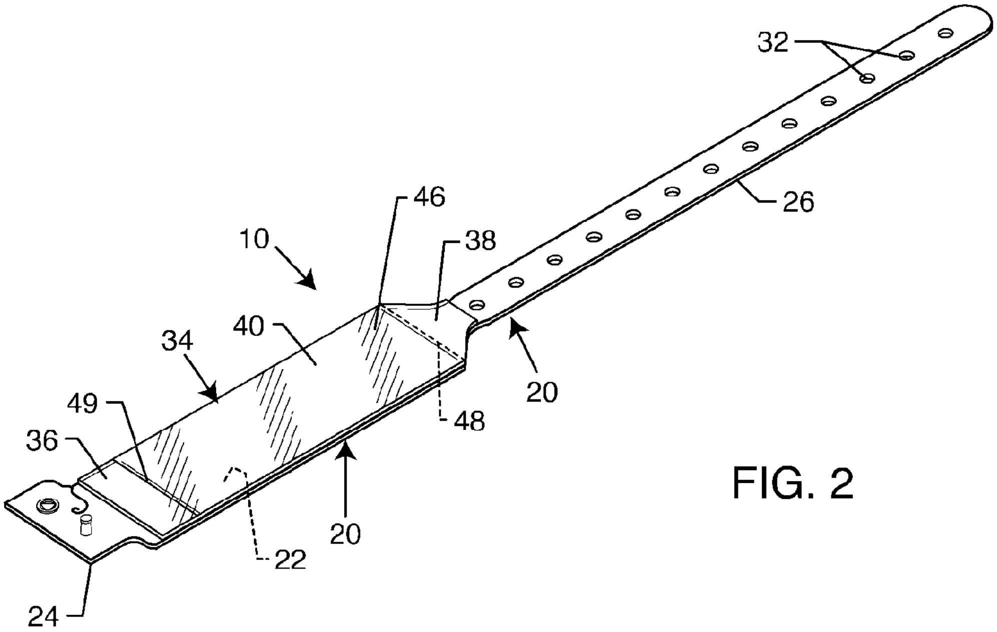
FIG. 2 is a top perspective view of a single identification bracelet having a sealable window in accordance with the invention, and showing opposite ends of an adhesive-backed transparent cover strip initially adhered to an underlying flexible band.
Figure 3:
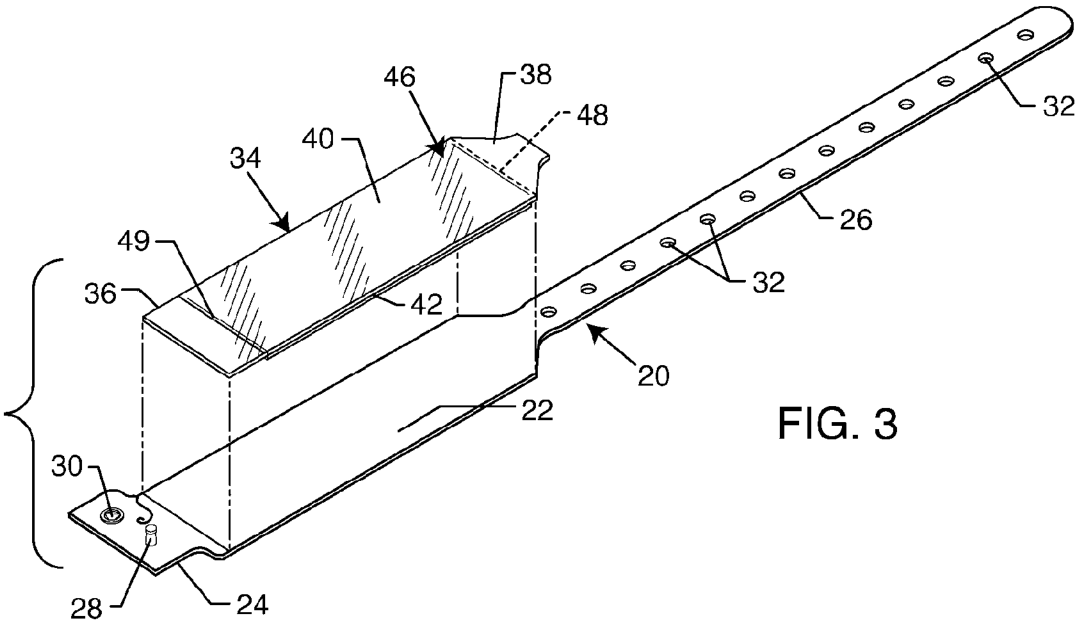
FIG. 3 is an exploded perspective view showing the adhesive-backed transparent cover strip in exploded relation to the underlying flexible band.

As shown generally in FIGS. 2-3, each identification bracelet 10 of the present invention comprises an elongated strap or band 20 having a single or multi-ply or multi-layer construction formed from a soft, smooth, non-abrasive, flexible and lightweight moisture-resistant or moisture-impervious, and stretch-resistant material of selected color, and shaped to define an upwardly presented information-bearing zone 22 thereon. In one preferred form, the band material comprises a multi-ply durable plastic strap including adhesive bonded layers (not shown) having a combined thickness on the order of about 10-12 mils. The information-bearing zone 22 is positioned longitudinally between a first band end 24 and a second band end 26, at least one of which includes fastener means adapted for shaping and retaining the band in a closed loop configuration (FIG. 12) of selected diametric size wrapped about the wrist or the like of a person or object to be associated therewith. Accordingly, the information-bearing zone 22 on the band 20 is independent of such fastener means.

The illustrative drawings show the first band end 24 to include fastener means such as snap-fit engageable male and female fastener components 28 and 30 adapted to interlock through a selected one of a series of longitudinally spaced fastener ports 32 formed in the second band end 26, as shown and described in more detail in U.S. Pat. No. 5,581,924 which is incorporated by reference herein. Such fastener components are beneficially designed for self-locking, and effectively permit removal of the bracelet 10 from a person's wrist or the like only by cutting and destroying the bracelet. Persons skilled in the art will recognize and appreciate that a variety of different fastener means and fastener constructions, such as adhesive fastener elements, and alternative mechanical fastener elements, may be used.

A transparent cover strip 34 is mounted onto the flexible band 20 in a position extending over or spanning the information-bearing zone 22 on the band. This transparent cover strip 34 is also formed from a lightweight and water-resistant or water-impervious and substantially transparent material such as a plastic film, and, in the preferred form, is backed by a thin layer of a transparent adhesive material such as a pressure-sensitive adhesive. In an initial configuration, opposite ends 36 and 38 of the adhesive-backed cover strip 34 are securely adhered to the flexible band 20 respectively at opposite ends of the underlying information-bearing zone 22. However, a central region of the cover strip 34, defining a transparent central window segment 40, is initially separated or spaced from the band and thus is not adhered thereto, by means of a thin peel-off paper-based release film 42. Thus, in the initial as-constructed configuration, the cover strip 34 has both ends firmly connected by the adhesive backing to the band 20 at opposite ends of the information-bearing zone 22, with the peel-off release film 42 separating the central window segment 40 from the underlying information-bearing zone 22 on the band 20. This initial as-constructed configuration is particularly suitable for convenient and economical production in the sheet form 14 as viewed in FIG. 1, wherein this form 14 includes multiple identification bracelets 10 in substantially side-by-side relation and adapted for individual snap-apart or tear-apart separation from the sheet form 14 along appropriate inter-bracelet lines of weakness such as perforation lines 44, when bracelet use is desired.

Figure 4:
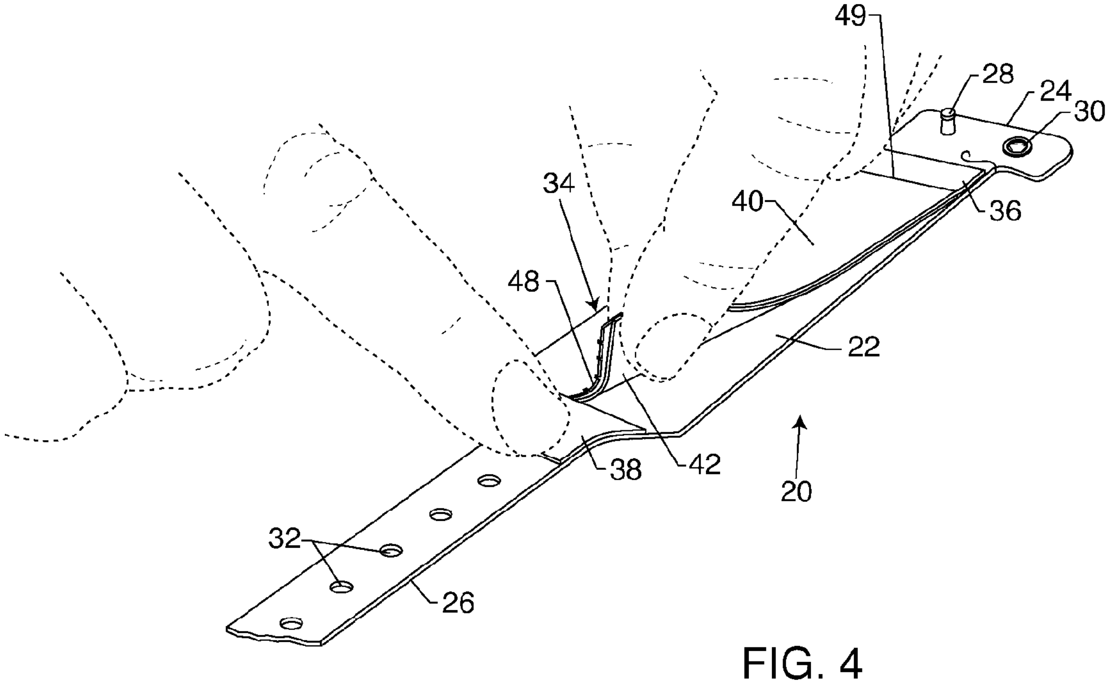
FIG. 4 is a top perspective view similar to FIG. 2, but depicting an initial step for manipulating the identification bracelet to separate or sever one end of the transparent cover strip from the underlying flexible band.
Figure 5:
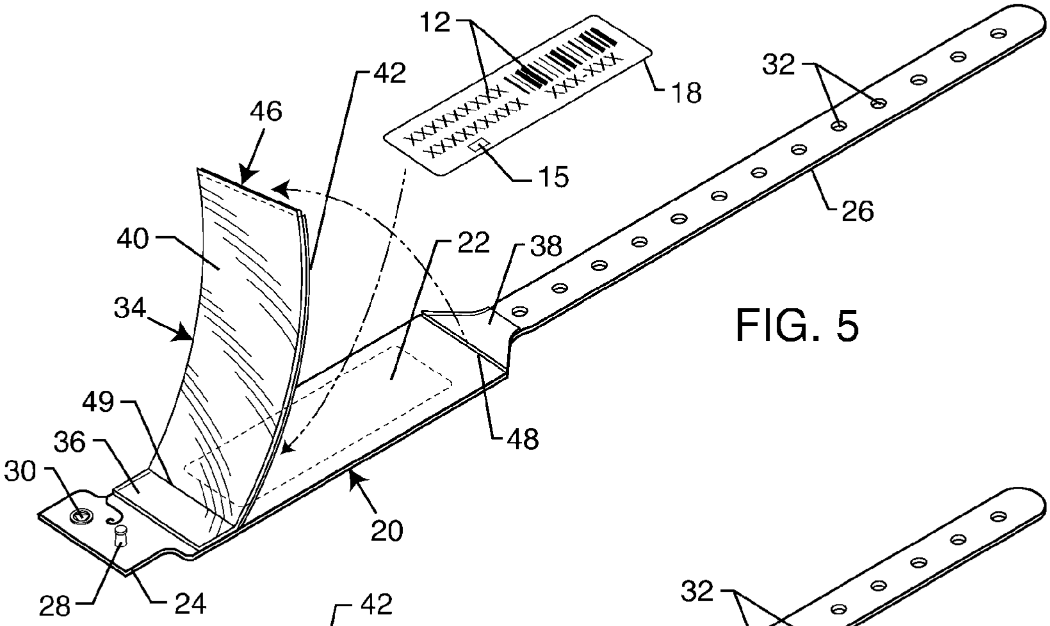
FIG. 5 is a top perspective view showing an identification card, tag or label in exploded relation to the identification bracelet with the protective cover strip in a raised position.

FIG. 4 shows initial manipulation of the identification bracelet 10 preparatory to addition of appropriate wearer-related information 12 to the information-bearing zone 22. As shown, the central window segment 40 can be separated from the adjacent adhesively anchored end 38 of the cover strip 34, as by tearing along a pre-formed line of weakness such as a perforation line 48 or the like formed in the cover strip. The thus-separated end 46 of the central window segment 40 can then be raised relative to the underlying information-bearing zone 22, effectively pivoting the window segment 40 upwardly about a hinge or fold line 49 adjacent the still anchored opposite end 36 of the cover strip as viewed in FIG. 5. This exposes the information-bearing zone 22 for receiving the wearer-related information 12, as by placement of the card, tag or label 18 thereon, or alternately by direct hand-written application of the wearer-related information on the information-bearing zone 22.

Figure 6:
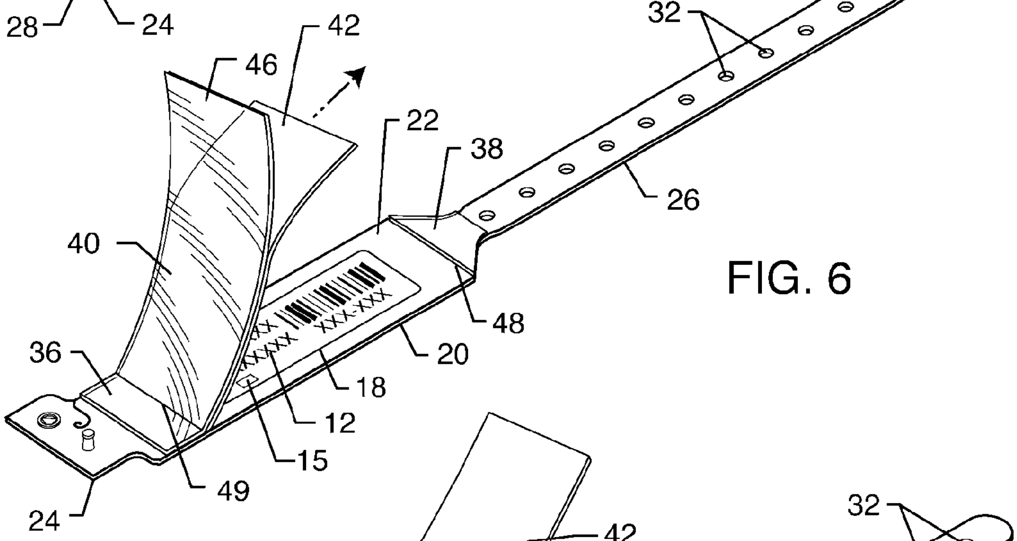
FIG. 6 is a further top perspective view illustrating peel-off separation of a protective paper or the like from the underside of the transparent cover strip to expose an adhesive film on the underside of said cover strip.
Figure 7:
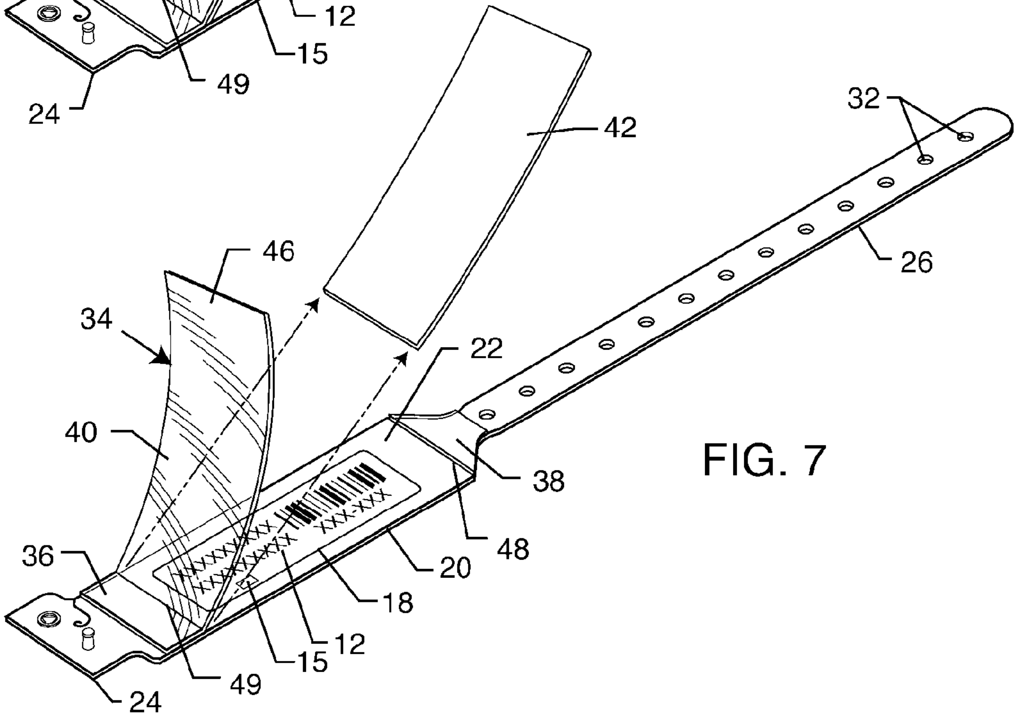
FIG. 7 is another top perspective view showing removal of the peel-off protective paper or the like for disposal, following peel-off separation from the cover strip.
Figure 8:
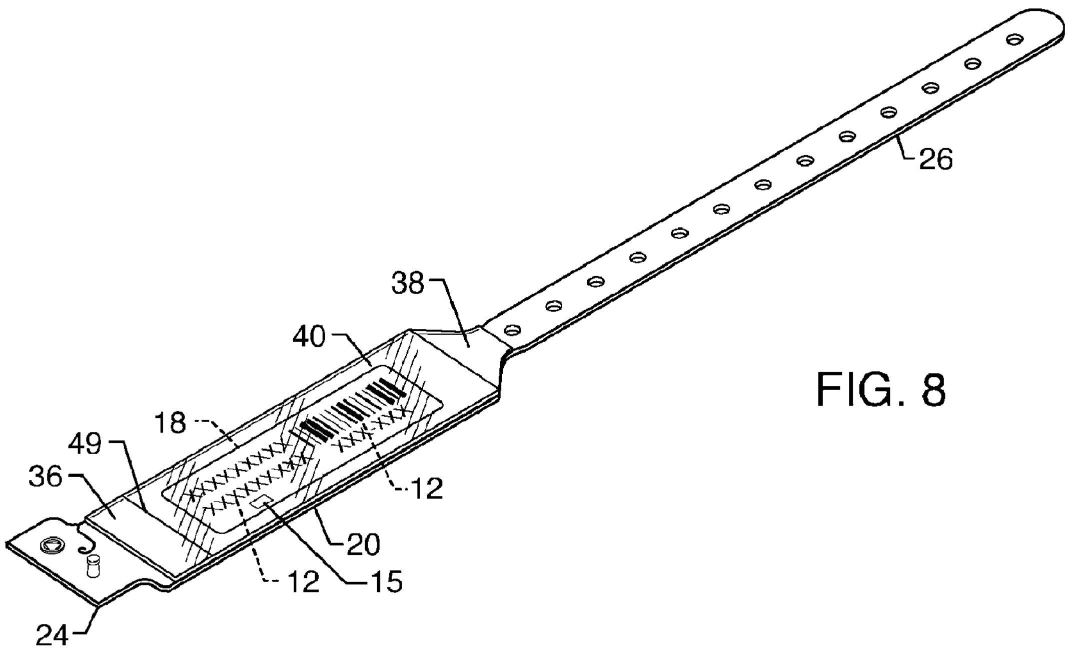
Figure 9:
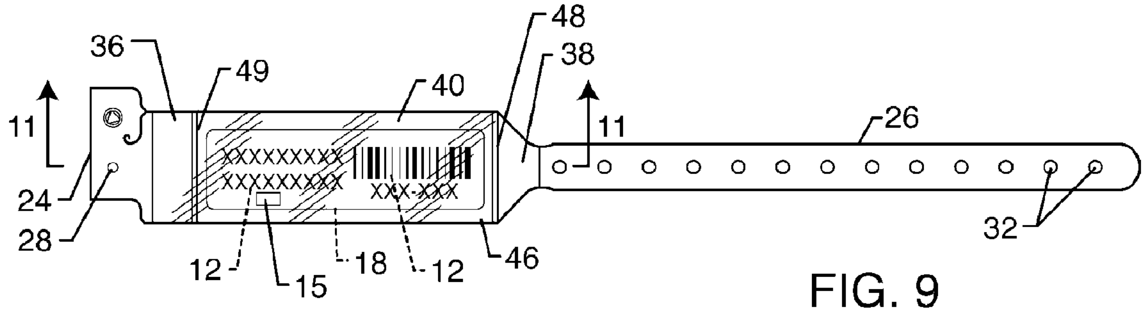
FIG. 9 is a top plan view of the identification bracelet of FIG. 8.
Figure 10:
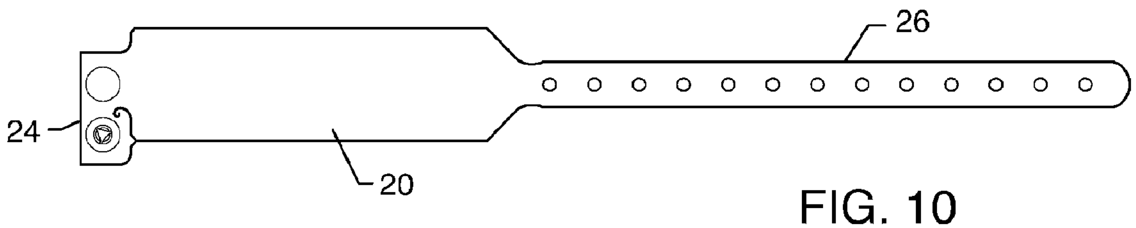
FIG. 10 is a bottom plan view of the identification bracelet.
Figure 11:
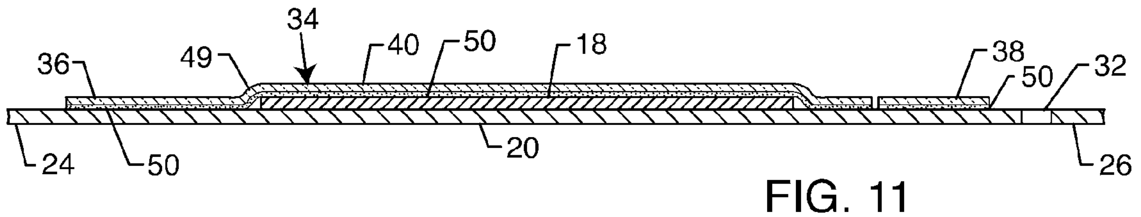
FIG. 11 is an enlarged fragmented vertical sectional view taken generally on the line 11-11 of FIG. 9.

With the window segment 40 in the raised position, the peel-off release paper-based film 42 is substantially exposed for easy access and removal (FIGS. 6-7), thereby exposing the thin-film transparent adhesive backing. In particular, FIG. 6 shows peel-off separation of the release film 42 from the window segment, and FIG. 7 shows removal of the peeled-off release film 42 for appropriate disposal. Upon subsequent downward displacement of the strip central window segment 40, the adhesive-backed window segment can be pressed and seated firmly onto the information-bearing zone 22 of the band 20 (FIGS. 8-9 and 11), with the adhesive backing 50 in intimate adhered engagement with the underlying band 20 as viewed best in FIG. 11. Importantly, the wearer-related information 12 applied to this zone 22 is positioned with a perimeter spaced inwardly from a perimeter of the zone 22, so that a moisture-impermeable hermetic seal perimeter circumscribing the information 12 is cooperatively defined by the window segment 40 and the underlying band 20. Thus, the window segment 40 and band 20 cooperatively form the sealable window encasing the wearer-related information 18 for reliable and accurate information read-out by human and/or machine means.

Persons skilled in the art will recognize and appreciate that alternative forms of the invention may be employed to achieve the desired moisture-impermeable hermetic seal perimeter circumscribing the wearer-related information 12 on the information-bearing zone 22 of the band 20. For example, in lieu of the pressure sensitive adhesive and peel-off release film 42 initially underlying the transparent central window segment 40, other techniques such as heat sealing of the central window segment 40 onto the underlying band 20 following placement of the wearer-related information 12 on the zone 22 may be used.

In use, the bracelet 10 thus incorporates the wearer-related information 12 viewable through the transparent central window segment 40. Importantly, this window segment 40 comprising a laminating element which cooperates with the underlying band 20 to hermetically encase the wearer-related information 12 on the information-bearing zone 22 is a manner that is protected against moisture ingress. The hermetic seal perimeter circumscribing the wearer-related information is sufficiently flexible to accommodate normal bending and use of the bracelet 10 in a closed loop configuration (FIG. 12) mounted onto the wrist or the like of a person or the like associated with the information 12. The thus-formed sealed window thereby safeguards the wearer-related information 12 against potentially damaging contact with moisture and other liquids, while permitting normal activities such as bathing and showering, etc.

Figure 13:
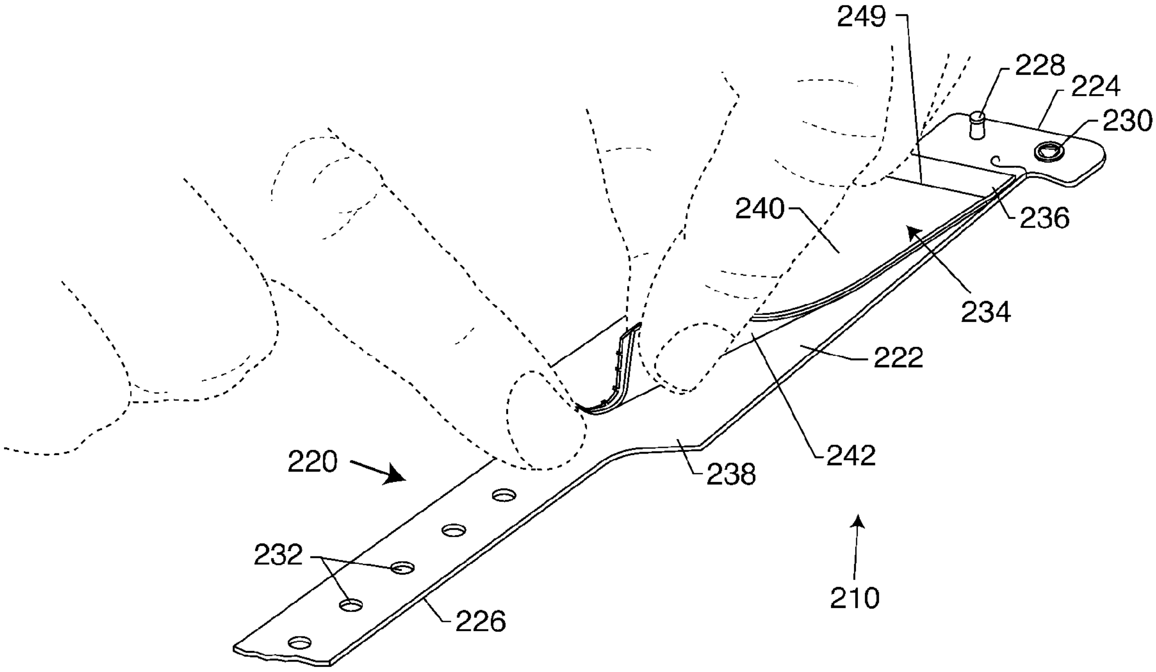
FIG. 13 is a fragmented top perspective view similar to FIG. 4, but depicting an alternative preferred form of the invention.

FIG. 13 depicts an alternative preferred form of the invention, wherein components similar to those shown and described in FIGS. 1-12 are identified by common reference numerals increased by 200. As shown, a modified identification bracelet 210 comprises an elongated flexible strap or band 220 shaped to define an upwardly presented information-bearing zone 222 positioned longitudinally between a first band end 224 having fastener components, such as the illustrative male and female snap-fit members 228 and 230, and a second band end 226 having multiple fastener ports 232 formed therein. A transparent cover strip 134 overlies the information-bearing zone 222 and is backed by a thin transparent adhesive layer or film for affixation to the band 220. In the configuration shown, opposite ends 236 and 238 of the cover strip 234 are adhered to the underlying band 220, with a transparent central window segment 140 defined between these adhered ends 236, 238. A peel-off, paper-based release film 242 is shown underlying the central window segment 240, to extend from a hinge line 249 proximate the adhered strip end 236 to a position spaced a short distance from the opposite end of the cover strip 234 thereby defining the opposite strip end 238 with exposed adhesive for initial adherence to the band 220.

In use, the adhered end 238 of the cover strip 234 can be lifted and separated from the underlying band 220, as viewed in FIG. 13. This exposes the information-bearing zone 222 for receiving and supporting the wearer-related information, all as shown and described previously herein with respect to FIGS. 1-12. Following placement of the wearer-related information on the zone 222, the release film 242 can be separated from the central window segment 240, followed in turn by adhesive seating and sealing of the window segment 240 and the associated strip end 238 with the underlying band 220. Importantly, the window segment 240 and cover strip end 238 effectively define an hermetically sealed perimeter circumscribing and thus protecting the wearer-related information, while visually exposing such information for human and/or machine communication.

Accordingly, the alternative embodiment shown in FIG. 13 also provides for initial adherence of both ends 236, 238 of the transparent cover strip 234 with the band 220, for simplified manufacturing of the bracelet 220 in sheet or roll form.

Figure 1:
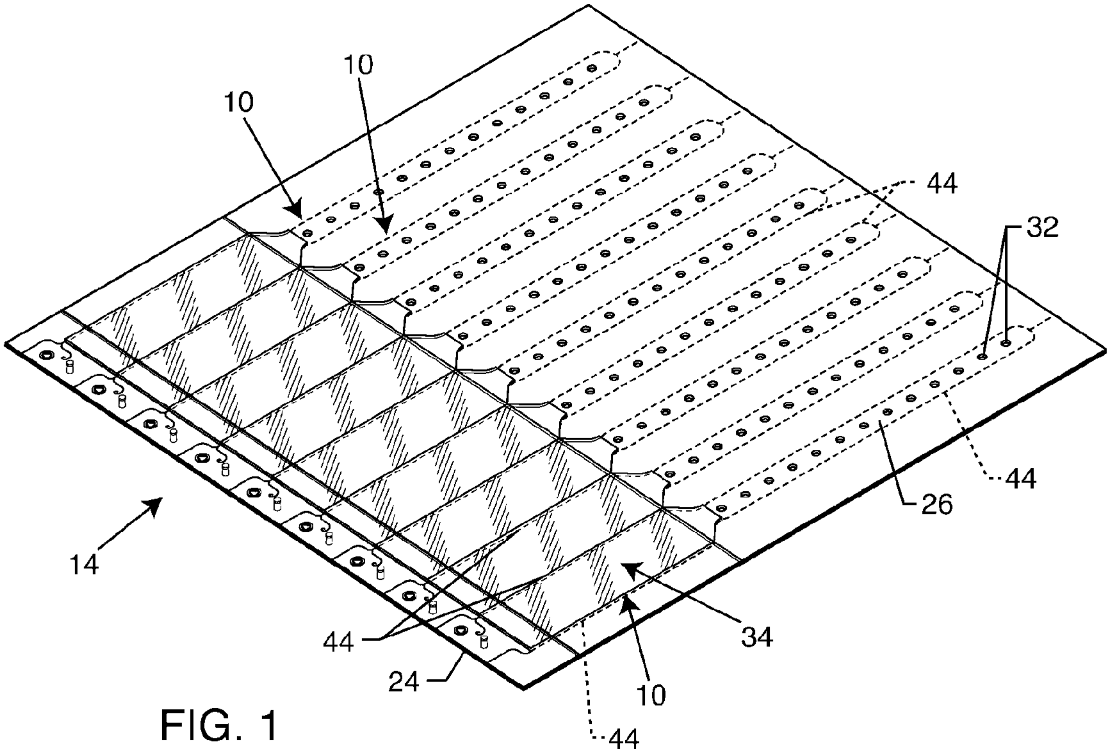
FIG. 1 is a top perspective view of a sheet form incorporating a plurality of separable identification bracelets each having a sealable window and constructed in accordance with the novel features of the invention.
Figures 14, 15, 16:
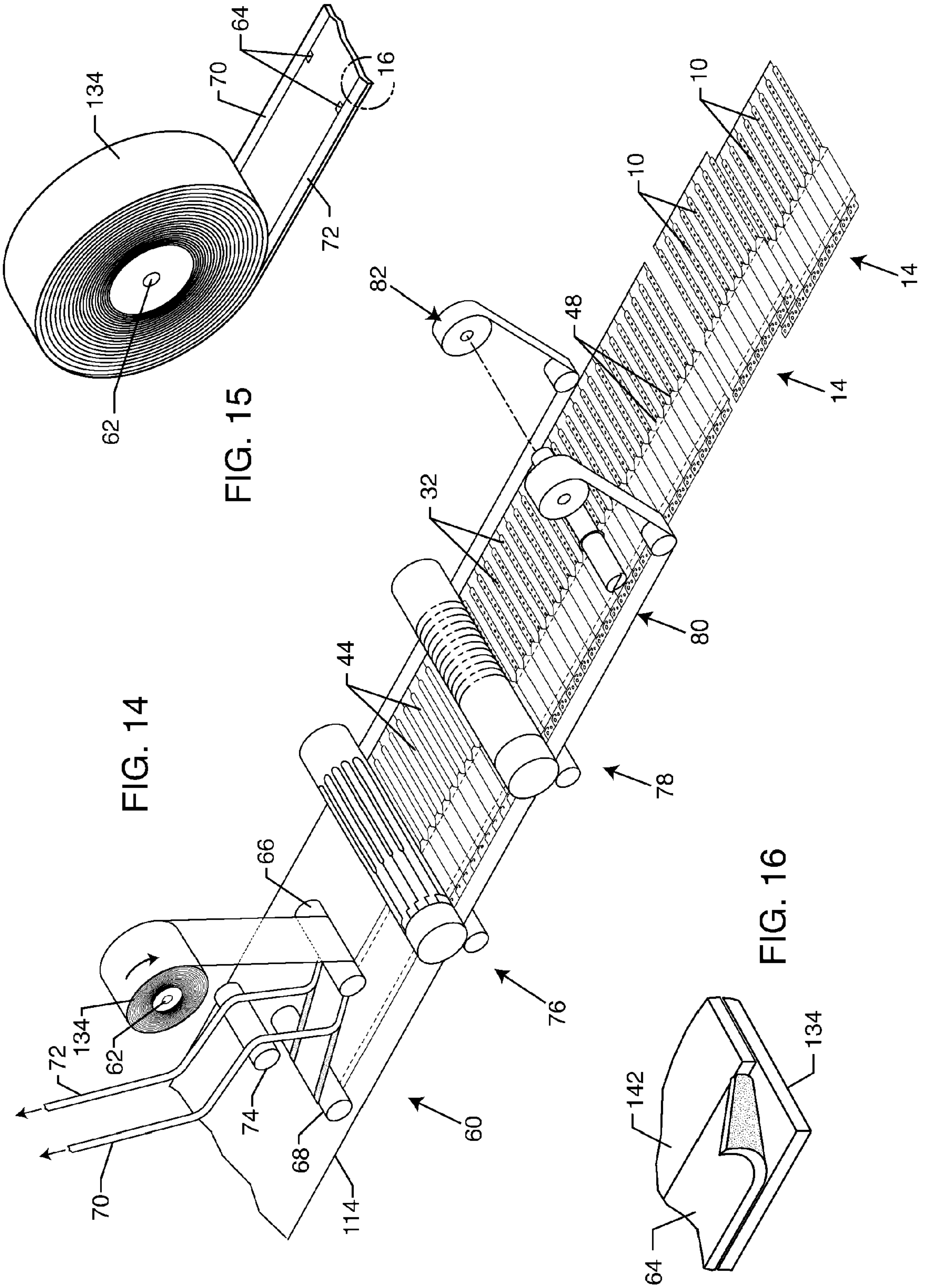
FIG. 14 is a somewhat schematic perspective view showing one exemplary production line process for producing the identification bracelet in sheet form.
FIG. 15 is a perspective view illustrating a supply reel carrying material used for the adhesive-backed transparent cover strip, for use in the production process of FIG. 14.
FIG. 16 is an enlarged fragmented perspective view corresponding generally with the encircled region 16 of FIG. 15.

FIGS. 14-16 illustrate one exemplary production process for manufacturing the identification bracelet 10 of the present invention in multi-bracelet sheets 14 as depicted in FIG. 1, although it will be understood that a similar production process may be employed for manufacturing the bracelet 210 as depicted in FIG. 13. In this regard, the bracelet construction wherein both of the opposite ends 36, 38 of the cover strip 34 are securely anchored as by adherence onto the underlying band 20 beneficially accommodates a variety of production processes without concern for an otherwise loose or free flap-type structure lifting prematurely to interfere with high volume production.

More specifically, FIG. 14 shows an elongated web 114 of suitable band-forming material that is conveyed as by drawing from a supply reel (not shown) or the like through a sequence of process stations. At an initial laminating station 60, an elongated web 134 of suitable cover strip-forming material is drawn from a supply reel 62 for adhesive placement onto the band-forming material 114. In this regard, FIGS. 15-16 show the supply reel 62 carrying the cover strip-forming material 134 having the transparent adhesive film applied to one side thereof and protectively covered by a peel-off release layer 142. This peel-off release layer 142 includes elongated cuts or slits 64 spaced inwardly short distances from the opposed edges thereof.

The cover strip-forming material 134 is drawn from the supply reel 62 over suitable guide reels 66 and 68 which guide and press the material 134 onto the underlying band-forming material 114. Importantly, thin edge strips 70 and 72 of the release layer 142 are separated from the material 134 by a waste roller 74, so that the opposite edges of the material 134 are pressed into secure adhered engagement with the band-forming material 114. These adhered opposite edges of the cover strip-forming material 134 correspond with the opposite ends 36, 38 of each cover strip 34, with the remaining central portion of the release layer 142 corresponding with the release film 42, all as previously shown and described herein.

From the laminating station 60, the partially underlying band-forming material 114 and the overlying cover strip-forming material 134 are drawn or transported further through a sequence of die cutting stations, such as an outline die station 76 for cutting the underlying material into the outline shape of a succession of individual bracelets 10 separable along adjoining lines of weakness such as perforations 44, and a hole cutting station 78 for cutting multiple fastener ports 32 in each bracelet 10. An additional perforation die station 80 then forms the line of weakness such as the perforation 48 between the central window segment 40 and one adhesively anchored end 38 of each cover strip 34.

Although rotary die elements are shown, it will be understood that other types of die elements, including non-rotary die elements, may be used.

A waste web station 82 separates any remaining marginal material from the elongated succession of bracelets 10 which can then be formed into the desired multi-bracelet sheets 14.

Figure 17:
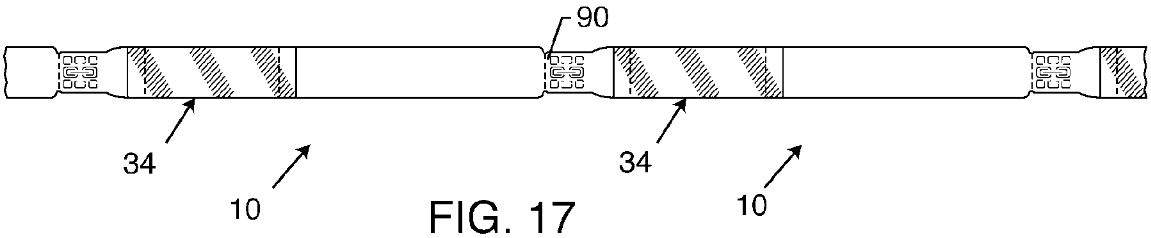
FIG. 17 is a plan view showing a succession of identification bracelets constructed in accordance with the invention, in end-to-end array.
Figure 18:
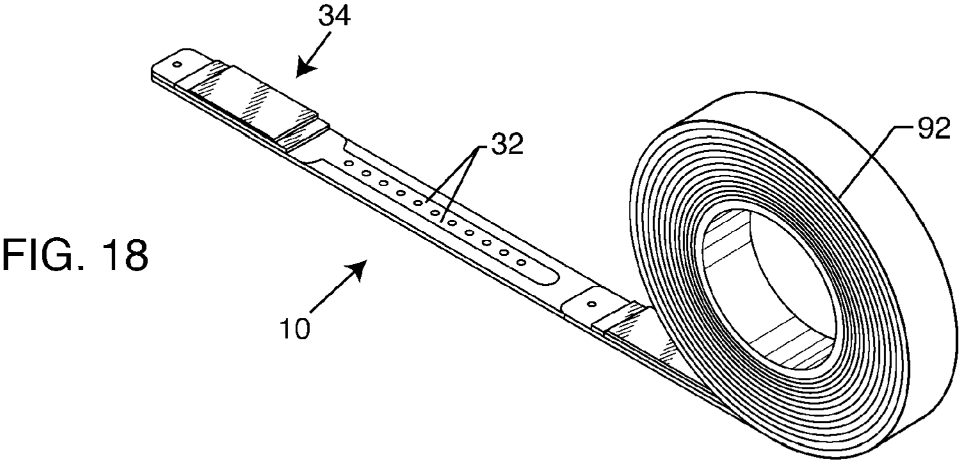
FIG. 18 shows the end-to-end bracelets of FIG. 17 carried on a supply reel.
Figure 19:
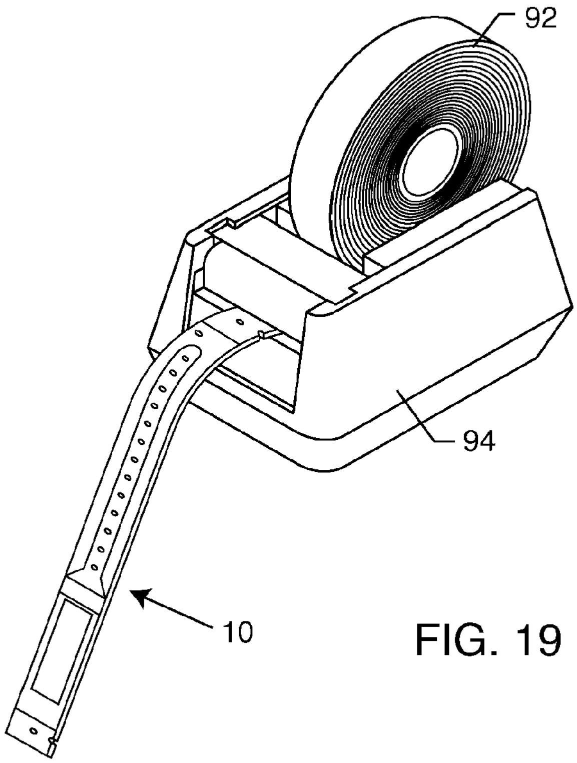
FIG. 19 illustrates a dispenser for dispensing the end-to-end bracelets of FIGS. 17-18 one at a time.

FIGS. 17-19 illustrate an alternative multi-bracelet construction, wherein individual identification bracelets 10 of the present invention are produced in end-to-end interconnected array adapted for tear-away separation along lines of weakness such as perforations 90. The end-to-end bracelets 10 can be assembled within a supply reel 92 (FIGS. 18-19) that can be mounted within a dispenser 94 for convenient draw-out dispensing of the bracelets 10 one at a time.

Irrespective of the production process and direction, i.e., side-by-side in multi-bracelet sheet form as viewed in FIG. 14, or end-to-end in multi-bracelet roll form as viewed in FIGS. 18-19, the cover strip 34 on each bracelet 10 is adhered securely at both ends 36, 38 thereof to the underlying band 20 whereby there are no free-ended flaps or similar structures that can limit production method or direction, and/or can caused production equipment to jam.

A variety of further modifications and improvements in and to the identification bracelet 10 of the present invention will be apparent to persons skilled in the art. Accordingly, no limitation on the invention is intended by the foregoing description and accompanying drawings, except as set forth in the appended claims.

What is claimed is:

1. An identification bracelet, comprising:

an elongated flexible band having first and second ends, and defining an information-bearing zone on one side thereof;

an adhesive-backed and substantially transparent cover strip defining a flexible central window segment between opposite strip ends, said opposite strip ends being initially adhered to said band generally at opposite ends of said information-bearing zone to position said central window segment in overlying relation to said information-bearing zone;

said central window segment including one end separable from said band to permit said window segment to be lifted upwardly relative to said band to expose said information-bearing zone to receive wearer-related information, said window segment being thereupon movable to a position overlying said information-bearing zone with at least a perimeter of said window segment sealingly adhered to said band for defining a sealed perimeter circumscribing the wearer-related information; and fastener means for retaining said band in a closed loop configuration.

2. The identification bracelet of claim 1 further including a peel-off release film carried by said central window segment to initially separate said central window segment from said band and thereby prevent adherence thereof to said information-bearing zone on said band, said release film being exposed for access and removal from said central window segment, when said central window segment is lifted upwardly relative to said band.

3. The identification bracelet of claim 1 wherein said one end of said central window segment is separable from one of said strip ends adhered to said band, to permit said one end of said window segment to be lifted upwardly relative to said band.

4. The identification bracelet of claim 1 wherein said band and said central window segment of said cover strip are formed from a substantially moisture-impervious material.

5. The identification bracelet of claim 1 wherein the wearer-related information comprises human-readable information.

6. The identification bracelet of claim 1 wherein the wearer-related information comprises machine-readable information.

7. The identification bracelet of claim 1 wherein the wearer-related information is carried by an RFID device.

8. The identification bracelet of claim 1 wherein the wearer-related information comprises bar code information.

9. The identification bracelet of claim 1 wherein the wearer-related information is applied to a card, tag or label, said card, tag or label having a size and shape for placement onto said information-bearing zone on said band.

10. The identification bracelet of claim 3 further including a line of weakness formed in said cover strip generally at said one end of said central window segment.

11. The identification bracelet of claim 1 further including a hinge line formed in said cover strip generally at an opposite end of said central window segment.

12. The identification bracelet of claim 1 wherein said information-bearing zone on said band is independent of said fastener means.

13. The identification bracelet of claim 1 wherein said fastener means comprises at least one fastener component mounted generally at at least one of said first and second ends of said band.

14. The identification bracelet of claim 1 wherein a plurality of said identification bracelets are assembled in a sheet form and each separable from said sheet form by tear-away separation along at least one line of weakness therebetween.

15. The identification bracelet of claim 1 wherein a plurality of said identification bracelets are assembled end-to-end and each separable along at least one line of weakness therebetween.

16. An identification bracelet, comprising:

an elongated flexible band formed from a substantially moisture-impervious material, said band having first and second ends, and defining an information-bearing zone on one side thereof;

an adhesive-backed and substantially transparent cover strip defining a flexible central window segment formed from a substantially moisture impervious material and extending between opposite strip ends, said opposite strip ends being adhered to said band generally at opposite ends of said information-bearing zone to position said central window segment in overlying relation to said information-bearing zone;

a peel-off release film carried by said central window segment to separate said central window segment from said band and thereby prevent adherence thereof to said information-bearing zone on said band;

said central window segment including one end separable from one of said strip ends along a line of weakness formed in said cover strip generally at said one end of said central window segment, to permit said window segment to be lifted upwardly relative to said band to expose said information-bearing zone to receive wearer-related information, and to facilitate access to and removal of said release film from said central window segment, said window segment being thereupon movable to a position overlying said information-bearing zone with at least a perimeter of said window segment sealingly adhered to said band for defining a sealed perimeter circumscribing the wearer-related information; and fastener means for retaining said band in a closed loop configuration.

17. The identification bracelet of claim 16 wherein the wearer-related information is selected from the group consisting essentially of human-readable and machine-readable information.

18. The identification bracelet of claim 16 wherein the wearer-related information is carried by an RFID device.

19. The identification bracelet of claim 16 wherein the wearer-related information comprises bar code information.

20. The identification bracelet of claim 16 wherein the wearer-related information is applied to a card, tag or label, said card, tag or label having a size and shape for placement onto said information-bearing zone on said band.

21. The identification bracelet of claim 16 further including a hinge line formed in said cover strip generally at an opposite end of said central window segment.

22. The identification bracelet of claim 16 wherein said information-bearing zone on said band is independent of said fastener means.

23. A sheet form comprising a plurality of said identification bracelets according to claim 16 arrayed in connected relation, each of said plurality of identification bracelets being adapted for separation along at least one line of weakness therebetween.

24. A supply reel comprising a plurality of said identification bracelets according to claim 16 arrayed in end-to-end connected relation, each of said plurality of identification bracelets being adapted for separation along a line of weakness therebetween.

25. An identification bracelet, comprising:

an elongated flexible band having first and second ends, and defining an information-bearing zone on one side thereof;

a transparent cover strip defining a flexible central window segment between opposite strip ends, said opposite strip ends being adhered to said band generally at opposite ends of said information-bearing zone to position said central window segment in overlying relation to said information-bearing zone;

said cover strip including a line of weakness disposed generally between said central window segment and one of said strip ends adhered to said band, said central window segment being separable along said line of weakness from said one strip end to permit said window segment to be lifted upwardly relative to said band to expose said information-bearing zone to receive wearer-related information, said window segment being thereupon movable to a position overlying said information-bearing zone and including adhesive means for sealingly adhering said window segment to said band along an hermetically sealed perimeter circumscribing the wearer-related information.

26. The identification bracelet of claim 25 further including fastener means for retaining said band in a closed loop configuration.

27. The identification bracelet of claim 25 wherein said band and said central window segment of said cover strip are formed from a substantially moisture-impervious material.

28. The identification bracelet of claim 25 wherein the wearer-related information is selected from the group consisting essentially of human-readable and machine-readable information.

29. The identification bracelet of claim 25 wherein the wearer-related information is carried by an RFID device.

30. The identification bracelet of claim 25 wherein the wearer-related information comprises bar code information.

31. The identification bracelet of claim 25 wherein the wearer-related information is applied to a card, tag or label, said card, tag or label having a size and shape for placement onto said information-bearing zone on said band.

32. A sheet form comprising a plurality of said identification bracelets according to claim 25 arrayed in connected relation, each of said plurality of identification bracelets being adapted for separation along at least one line of weakness therebetween.

33. A supply reel comprising a plurality of said identification bracelets according to claim 25 arrayed in end-to-end connected relation, each of said plurality of identification bracelets being adapted for separation along a line of weakness therebetween.

34. In an identification bracelet comprising an elongated flexible band having first and second ends, an information bearing zone defined on one side thereof, and fastener means for retaining the band in a closed loop configuration, a method of protecting wearer-related information on the information-bearing zone, said method comprising the steps of:

Providing a transparent cover strip defining a flexible central window segment between opposite strip ends;

Adhering the opposite strip ends of the cover strip to the band generally at opposite ends of said information-bearing zone;

Lifting the central window segment relative to said band at a first of the opposite strip ends to expose the information-bearing zone;

Applying wearer-related information to the exposed information-bearing zone on the band; and Returning the window segment to a position overlying the information-bearing zone and sealingly adhering the window segment to the band along an hermetically sealed perimeter circumscribing the information-bearing zone and the wearer-related information thereon.

35. The method of claim 34 further including the step of separating the central window segment from one of the opposite strip ends mounted to the band prior to said lifting step.

36. The method of claim 34 wherein the step of adhering the opposite strip ends to the band comprises an adhesive mounting step.

37. The method of claim 34 wherein the cover strip is backed with a transparent adhesive, and further including the step of initially lining the central window segment with a peel-off strip for initially preventing adhesion of the central window segment with the band, and removing the peel-off strip subsequent to said lifting step.

38. The method of claim 35 further including the step of forming a line of weakness in the cover strip between the central window segment and one of the strip opposite ends mounted to the band, said separating step comprising severing the cover strip along the line of weakness.

39. The method of claim 34 further including the step of forming a hinge line between the central window segment and a second of the opposite strip ends.

40. The method of 34 wherein said applying step comprises manually applying the wearer-related information to the information-bearing zone.

41. The method of claim 34 wherein said applying step comprises applying the wearer-related information to a card, tag or label having a size and shape for placement onto said information-bearing zone on said band, and placing the card, tag or label onto the band.

42. A method of producing a succession of elongated identification bracelets, comprising the steps of:

conveying an elongate we of band-forming material along a production path;

adhering opposite ends of transparent cover strip-forming material onto the web of band-forming material; and subdividing the web of band-forming material and cover strip-forming material into a plurality of elongated flexible identification bracelets each having a transparent cover strip having opposite ends adhered to an elongated flexible band, and with said transparent cover strip further including a central window segment formed between said opposite ends and overlying an information-bearing zone on said band;

said subdividing step including forming at least one line of weakness between adjoining bracelets.

43. The method of claim 42 wherein said plurality of elongated flexible bracelets are formed side-by-side.

44. The method of claim 42 wherein said plurality of elongated flexible bracelets are formed end-to-end.

45. The method of claim 42 wherein the opposite ends of the transparent cover strip-forming material are adhesively secured to said web of band-forming material.

46. The method of claim 42 the cover strip-forming material is backed with a transparent adhesive, and further including the step of initially lining the cover strip-forming material between the opposite ends thereof with a peel-off strip for initially preventing adhesion with the band.

47. The method of claim 42 further including the step of forming a line of weakness in the cover strip-forming material generally adjacent one of the opposite ends thereof.

* * * * *